United States Patent [19]

Doyle

[11] Patent Number: 5,750,344
[45] Date of Patent: May 12, 1998

[54] METHOD FOR SELECTION OF BIOLOGICALLY ACTIVE PEPTIDE SEQUENCES

[76] Inventor: Michael V. Doyle, 4560 Horton St., Emeryville, Calif. 94608

[21] Appl. No.: 538,911

[22] Filed: Oct. 4, 1995

Related U.S. Application Data

[63] Continuation of Ser. No. 69,352, May 28, 1993, abandoned.

[51] Int. Cl.$^6$ .............................. G12Q 1/64; G01N 33/53
[52] U.S. Cl. .................... 435/6; 435/5; 435/7.1; 435/7.2; 435/7.21; 435/7.3; 435/7.32; 435/7.37; 435/7.5; 435/962; 436/501; 436/518
[58] Field of Search ............................ 435/5, 6, 7.1, 7.2, 435/7.21, 7.3, 7.32, 7.37, 7.5, 962; 436/501, 518

[56] References Cited

FOREIGN PATENT DOCUMENTS 9119818  12/1991  WIPO .
9200091  1/1992  WIPO .

OTHER PUBLICATIONS

Christian et al J. Mol. Biol. 227 pp. 711–718 (1992) "Simplified Methods for Construction, Assessment and Rapid Screening of Peptide Librerics in Bacteiophage".

Parmley et al Gene 73 pp. 305–318 (1988) "Antibody–Selectable Fila Mentous Fd Phage Vectors: Affinity Purification of Forget Genes".

*Primary Examiner*—Lora M. Green
*Attorney, Agent, or Firm*—Grant D. Green; Sharon M. Fujita; Robert P. Blackburn

[57] ABSTRACT

An improved method for determining binding compounds from a mixture of similar compounds, particularly a phage peptide library, is provided. The method comprises contacting a mixture of candidate compounds with a target molecule presented on two or more different substrates.

13 Claims, No Drawings

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 85 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: misc_feature
        ( B ) LOCATION: 24..68
        ( D ) OTHER INFORMATION: /function="Random base sequence ( N N S )"
        / label= Randomer ( x i ) SEQUENCE DESCRIPTION: SEQ ID NO:1:

```
CTTTCTATTC TCACTCCGCT GAANNSNNSN NSNNSNNSNN SNNSNNSNNS NNSNNSNNSN    60

NSNNSNNSCC GCCTCCACCT CCACC                                          85
```

( 2 ) INFORMATION FOR SEQ ID NO:2:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: misc_feature
        ( B ) LOCATION: 22..66
        ( D ) OTHER INFORMATION: /function="Inosine"
        / standard_name= "Inosine"

/ label= Inosine ( x i ) SEQUENCE DESCRIPTION: SEQ ID NO:2:

GGCCGGTGGA GGTGGAGGCG GNNNNNNNNN NNNNNNNNNN NNNNNNNNNN NNNNNNNNNN    60

NNNNNNTTCA GCGGAGTGAG AATAGAAAGG TAC    93

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Region
        ( B ) LOCATION: 3..17
        ( D ) OTHER INFORMATION: /label=RandomPeptide
        / note= ""Xaa"refers to any natural amino acid.
        This domain is a random pep..."

( x i ) SEQUENCE DESCRIPTION: SEQ ID NO:3:

Ala Glu Xaa Xaa Xaa Xaa Xaa Xaa Xaa Xaa Xaa Xaa Xaa Xaa Xaa Xaa
1               5                           10                          15

Xaa Pro Pro Pro Pro Pro Pro
            20

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:4:

GCTGCCCGAG AGATCTGTAT ATATGAGTAA ACTTGG    36

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:5:

GCAGGCTCGG GAATTCGGGA AATGTGCGCG GAACCC    36

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (x i) SEQUENCE DESCRIPTION: SEQ ID NO:6:

AAACTTCCTC ATGAAAAAGT C                                           21

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:7:

AGAATAGAAA GGTACCACTA AAGGA                                       25

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:8:

TTTAGTGGTA CCTTTCTATT CTCACTCGGC CGAAACTGT                        39

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:9:

AAAGCGCAGT CTCTGAATTT ACCG                                        24

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:10:

TCGAAAGCAA GCTGATAAAC CG                                          22

(2) INFORMATION FOR SEQ ID NO:11:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:11:

ACAGACAGCC CTCATAGTTA GCG    23

( 2 ) INFORMATION FOR SEQ ID NO:12:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:12:

Ala Glu Cys Leu Asn Gly Gly Thr Ala Val Ser Asn Lys Tyr Phe Ser
1               5                   10                  15

Asn Ile His Trp Cys Asn
            20

( 2 ) INFORMATION FOR SEQ ID NO:13:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

Ala Glu Ser Gln Thr Gly Thr Leu Asn Thr Leu Phe Trp Asn Thr Leu
1               5                   10                  15

Arg ( 2 ) INFORMATION FOR SEQ ID NO:14:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( x i ) SEQUENCE DESCRIPTION: SEQ ID NO:14:

Ala Glu Trp His Pro Gly Leu Ser Phe Gly Ser Tyr Leu Trp Ser Lys
1               5                   10                  15

Thr ( 2 ) INFORMATION FOR SEQ ID NO:15:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( x i ) SEQUENCE DESCRIPTION: SEQ ID NO:15:

```
Ala Glu Met His Arg Ser Leu Trp Glu Trp Tyr Val Pro Asn Gln Ser
 1               5                  10                  15
Ala
```

( 2 ) INFORMATION FOR SEQ ID NO:16:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( x i ) SEQUENCE DESCRIPTION: SEQ ID NO:16:

```
Ala Glu Pro Leu Asp Leu Trp Ser Leu Tyr Ser Leu Pro Pro Leu Ala
 1               5                  10                  15
Met
```

( 2 ) INFORMATION FOR SEQ ID NO:17:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( x i ) SEQUENCE DESCRIPTION: SEQ ID NO:17:

```
Ala Glu Ser Ser Leu Trp Arg Ile Phe Ser Pro Ser Ala Leu Met Met
 1               5                  10                  15
Ser
```

( 2 ) INFORMATION FOR SEQ ID NO:18:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( x i ) SEQUENCE DESCRIPTION: SEQ ID NO:18:

```
Ala Glu Ser Ser Leu Trp Thr Arg Tyr Ala Trp Pro Ser Met Pro Ser
 1               5                  10                  15
Tyr
```

( 2 ) INFORMATION FOR SEQ ID NO:19:

```
    ( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( x i ) SEQUENCE DESCRIPTION: SEQ ID NO:19:

Ala  Glu  Pro  Ala  Leu  Leu  Asn  Trp  Ser  Phe  Phe  Phe  Asn  Pro  Gly  Leu
    1                   5                        10                       15

His ( 2 ) INFORMATION FOR SEQ ID NO:20:

( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( x i ) SEQUENCE DESCRIPTION: SEQ ID NO:20:

Ala  Glu  Pro  Met  Pro  His  Ser  Leu  Asn  Phe  Ser  Gln  Tyr  Leu  Trp  Tyr
    1                   5                        10                       15

Thr ( 2 ) INFORMATION FOR SEQ ID NO:21:

( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( x i ) SEQUENCE DESCRIPTION: SEQ ID NO:21:

Ala  Glu  Ser  Leu  Pro  Thr  Leu  Thr  Ser  Ile  Leu  Trp  Gly  Lys  Glu  Ser
    1                   5                        10                       15

Val
```

METHOD FOR SELECTION OF BIOLOGICALLY ACTIVE PEPTIDE SEQUENCES

This application is a continuation of application Ser. No. 08/069,352, filed May 28, 1993 now abandoned.

TECHNICAL FIELD

This invention pertains to the field of molecular biology and drug discovery. More particularly, this invention pertains to methods for screening libraries of compounds against a target (e.g., receptor or ligand), either soluble or surface-bound.

BACKGROUND OF THE INVENTION

A primary goal of drug discovery is to identify biologically active molecules that have practical clinical utility. The general approach taken by molecular biologists has been to initially identify a biological activity of interest, and then purify the activity to homogeneity. Next, assuming the molecule is a protein, the protein is sequenced and the sequence information used to generate synthetic DNA oligonucleotides that represent potential codon combinations that encode the protein of interest. The oligonucleotide is then used to probe a cDNA library derived from messenger RNA that was in turn derived from a biological source that produced the protein. The cDNA sequence so identified may be manipulated and expressed in a suitable expression system.

A second, more recent approach, termed expression cloning, avoids purifying and sequencing the protein of interest, as well as generating oligonucleotide probes to screen a cDNA library. Rather this procedure consists of initially ascertaining the presence of a biologically active molecule, generating cDNA from messenger RNA and directly cloning the cDNA into a suitable expression vector. The vector is typically an expression plasmid that is transfected or micro-injected into a suitable host cell to realize expression of the protein. Pools of the plasmid are assayed for bioactivity, and by narrowing the size of the pool that exhibits activity, ultimately a single clone that expresses the protein of interest is isolated.

Aside from the above approaches, it is known that bioactive molecules other than proteins are constantly being isolated and screened in large numbers using traditional screening regimens known to those that work in this field. Additionally, after a drug is identified and its chemical structure elucidated, attempts are made to synthesize more active versions of the drug by rational drug design or medicinal chemistry approaches.

Previously, it was suggested that an "epitope library" might be made by cloning synthetic DNA that encodes random peptides into filamentous phage vectors. Parmley and Smith, *Gene* (1988) 73:305. It was proposed that the synthetic DNA be cloned into the coat protein gene III because of the likelihood of the encoded peptide becoming part of pIII without significantly interfering with pIII's function. It is known that the amino terminal half of pIII binds to the F pilus during infection of the phage into *E. coli*. It was suggested that such phage that carry and express random peptides on their cell surface as part of pIII may provide a way of identifying the epitopes recognized by antibodies, particularly using antibody to affect the purification of phage from the library. Parmley and Smith, *Gene* (1988) 73:305. Devlin, PCT W091/18980 (incorporated herein by reference) described a method for producing a library consisting of random peptide sequences presented on filamentous phage. The library can be used for many purposes, including identifying and selecting peptides that have a particular bioactivity. An example of a ligand binding molecule would be a soluble or insoluble cellular receptor (i.e., a membrane bound receptor), but would extend to virtually any molecule, including enzymes, that have the sought-after binding activity. Description of a similar library is found in Dower et al., W091/19818. The present invention provides a method for screening such libraries (and other libraries of peptides) to determine bioactive peptides or compounds. Kang et al., W092/18619 disclosed a phage library prepared by inserting to the pVIII gene.

Previous investigators have shown that the outer membrane protein, LamB, of *E. coli* can be altered by genetic insertion to produce hybrid proteins having inserts up to about 60 amino acid residues. A. Charbit, et al., *Gene* (1988) 70:181. The authors suggest that such constructs may be used to produce live bacterial vaccines. See also, A. Charbit, et al., *EMBO J.* (1986) 5(11):3029; and A. Charbit et al., *J Immunol* (1987) 139(5):1658.

The procedures that are presently used to identify protein bioactive molecules, as well as small molecular weight molecules, require a significant commitment of resources which often limit the progress of such projects. Thus, other methods that facilitate the identification of bioactive molecules are keenly sought after, and would have wide applicability in identifying medicaments of significant practical utility.

DISCLOSURE OF THE INVENTION

One aspect of the invention is a method for screening a library of random peptides to identify bioactive peptides. The method comprises screening the library against a target on a first substrate, screening the results of the first screening on the target on a second substrate different from the first substrate, and (if desired) repeating the screening cycle one or more times. The target may be immobilized on the first and second substrates, or may be screened in soluble form followed by immobilization to the substrate. One may additionally screen against the target on a third substrate, and may use two or more similar targets to identify compounds which bind in common.

MODES OF CARRYING OUT THE INVENTION

A. Definitions

The term "mixture of similar compounds" refers to a mixture of different compounds having similar characteristics, from which a compound having desired binding characteristics may be selected. The similarity between compounds in the mixture will preferably relate to structure. For example, a mixture of different octapeptides constitutes a mixture of similar compounds within the scope of this definition. A series of diazepins in one solution, which differ in the length of a side chain, or number and position of halogen substituent, for example, also constitutes a "mixture of similar compounds" within the scope of this definition. In general, the mixture will contain at least 10 different compounds, and may contain $10^{10}$ or more. Presently preferred mixtures are random peptide and/or peptoid libraries.

The term "random peptide library" refers to a mixture of peptides from which candidate binding peptides may be selected. The random peptides may range in length from dimers to 100mers or more in length, but are preferably at least about 5 amino acids in length, more preferably at least about 7 amino acids in length, and most preferably at least about 15 amino acids in length. The random peptides will preferably be less than about 50 amino acids in length, more preferably less than 40 amino acids in length, and most preferably less than about 30 amino acids in length. The peptide, of whatever length, may be provided as a fusion protein or peptide, expressed in conjunction with a carrier protein (e.g., as a terminal portion of the pIII protein in M13). The random peptide may also be embedded at one or more locations within a protein fused to the carrier protein. The term "random" indicates only the most typical preparation of the library, and does not require that the composition may not be known: thus, one may prepare a mixture of precisely known composition if desired, and employ the method of the invention simply as a parallel screening procedure. Examples of biological random peptide libraries include, for example, without limitation, the phage display libraries described by Devlin, W091/18980, Dower et al., W091/19818, and Kang et al., W092/18619, all incorporated herein by reference. Other suitable biological random peptide libraries may be prepared by expressing random DNA fused to DNA encoding signal peptides which direct export of the peptide from the transfected host cell. The peptides are then collected from the culture supernatant. If desired, the peptides may also be provided with a membrane "anchor" (and optionally a spacer peptide), thus providing for display on the host cell surface. Alternatively, random DNA or RNA may be translated in a cell-free system, e.g., based on microsomes.

The term "target" refers to the molecule for which a binding peptide, peptoid, or other compound capable of binding thereto is desired. Suitable targets include, without limitation, cell surface receptors, cell surface antigens, enzymes, and other effector molecules. The method of the invention is most useful when the target may be expressed on the surface of a host cell. Many suitable targets are incorporated into cell membranes or cell walls, and are difficult or impossible to isolate in active form. However, the method of the invention permits one to express the target in its native form (or a form similar thereto) and screen for binding, while eliminating the background binding which would otherwise prevent or mask detection of compounds binding to the target. One may also express intracellular targets (e.g., cytoplasmic receptors, G-proteins, etc.) on the host cell surface to facilitate screening. The method of the invention may be applied to soluble targets which may be immobilized temporarily, e.g., for separation from non-specifically binding compounds. For example, one may screen against a soluble receptor, capturing the receptor after binding by using an immobilized antibody specific for the receptor. This step may be alternated with screening against soluble receptor immobilized by a different method (e.g., using biotin-avidin or magnetic interactions), or with screening against an immobilized receptor (e.g., an intact cell surface receptor).

The term "substrate" as used herein refers to the surface to which the target is attached or incorporated, either before or after contact with the mixture of similar compounds. The substrate preferably comprises a host cell which either normally expresses or has been transformed to express the target. However, the substrate may also (or alternatively) comprise a target immobilized on a solid support, such as, for example, a resin column support. The substrate may alternatively comprise a support with means for immobilizing the target following contact with the mixture of compounds (e.g., a column derivatized with antibodies specific for the target, or derivatized with antibodies specific for an antibody which binds the target). Presently preferred substrates are mammalian cells (such as COS cells, CHO cells, and 293 human kidney epithelial cells), insect cells, yeast, and bacteria (especially *E. coli*).

B. General Method

Described herein is a method for screening a mixture of compounds, particularly useful for identifying binding compounds from libraries consisting of random peptide sequences. This method may be referred to as "panning" for compounds. Traditional panning methods attempt to isolate compounds by affinity for a single substrate, for example, by one or more contacts with a target. The traditional methods may be sufficient in cases where the target is a pure substance, or is capable of binding with an affinity higher than that of any background compound. However, it is often not possible to isolate or purify the target (e.g., in the case of many transmembrane receptors, purification of which require complete denaturation and irreversible inactivation). Panning against whole cells is problematic because one tends to select compounds having an affinity for the binding moiety present in highest concentration (e.g., other surface receptors, carbohydrates, and the like). Further, it appears that some moieties may intrinsically be capable of binding a peptide with higher affinity than other moieties (for example, some receptors may have a deep cleft which permits maximal interaction with a peptide).

The method of the invention may be used to pan against whole cells, even where the exact nature of the target is unknown. In general, the method comprises panning a mixture of similar compounds against a first substrate which contains the desired target (or is capable of binding the target), followed by separating the binding compounds and panning them against an alternate substrate which also contains the desired target. By maximizing the disparity between the first and second substrates, one may minimize the interference due to background binding, and thus eliminate compounds which bind primarily to non-targets. Thus, the invention permits one to screen for compounds having an affinity for a particular target, even in the presence of non-targets present in higher concentration.

In the practice of the invention, one first provides a mixture of compounds to be tested. Libraries of peptides are preferably prepared by biological methods, for example as a phage display library (e.g., Devlin, W091/18980). Selection of the precise form of library is dictated more by the target system than by the panning procedure claimed herein.

The substrates are then selected. The substrates should be capable of providing the target, preferably in an easily accessible form on the surface. Ideally, two substrates are selected which are as different as possible. This minimizes the possibility of selected compounds which bind to a non-target that is common to both substrates. For example, one may select a mammalian cell line for the first substrate, and immobilize the target on a solid phase resin for the second substrate. The target may be immobilized before or after contact with the compounds being screened, e.g., by labeling the target with biotin and immobilizing on an avidin column, or using antibodies specific for the target. Where the target is not easily purified or immobilized, one may select pairs such as mammalian cell:insect cell, mammalian cell:yeast, yeast:bacteria., and the like. A presently preferred method of the invention utilizes mammalian cells (e.g., COS cells) and baculovirus-infected Sf9 insect cells as the two substrates.

The substrates are preferably adhered to a solid surface to facilitate washing. Suitable surfaces include microwell plates, culture dishes, and the like. Alternatively, one may use nonadherent substrates (e.g., yeast and bacteria) in combination with a filter or other means capable of retaining the substrate cells during wash steps. It is presently preferred to wash by centrifugation. One may employ a substrate which naturally presents the target, or may use substrates transformed to express the target.

Depending on the host cell used, transformation is done using standard techniques appropriate to such cells. The preferred method is electroporation in a low conductivity solution as described by W. J. Dower et al., *Nuc Acids Res* (1988) 16:6127. Commercially available electroporation machines may be utilized, such as, for example those made by BTX. Other methods, however, may also be used. For example, the calcium treatment employing calcium chloride, as described by S. N. Cohen et al., *Proc Natl Acad Sci (USA)* (1972) 69:2110, and modifications as described by D. Hanahan, *J Mol Biol* (1983) 166:557–580 are used for procaryotes or other cells which contain substantial cell wall barriers. Several transfection techniques are available for mammalian cells without such cell walls. The calcium phosphate precipitation method of Graham and Van Der Eb, *Virology* (1978) 52:546 is one method. Transfection can be carried out using a modification (Wang et al., *Science* (1985) 228:149) of the calcium phosphate co-precipitation technique. Another transfection technique involves the use of DEAE-dextran (L. M. Sompayrac et al., *Proc Natl Acad Sci USA* (1981) 78:7575–7578). Alternatively, one may transfect cells by lipofection, using a lipid matrix to transport plasmid DNA into the host cell (P. L. Felgner et al., *Proc Natl Acad Sci (USA)* (1987) 84:7413). The lipid matrix Lipofectin® is available from BRL.

If the binding compound is part of a fusion protein, preferably a filamentous viral surface protein, the presence of the random peptide sequence may be indicated by the binding of virus to a chosen target molecule, and separating bound and unbound virus. In this way, virus that contains the random peptide of interest may be isolated, and subsequently amplified by infection of a suitable host cell. Confirmation that the virus encodes a random sequence, as well as the predicted amino acid sequence, can be obtained using standard techniques, including the polymerase chain reaction, and DNA sequencing, respectively.

Each of the above purification techniques may be repeated multiple times to enrich for the virus that encodes the random peptide of interest.

C. Examples

The examples presented below are provided as a further guide to the practitioner of ordinary skill in the art, and are not to be construed as limiting the invention in any way.

EXAMPLE 1

(Oligonucleotides Encoding Random Peptides)

Oligonucleotides having the following structure were synthesized, and purified using methods known in the art:

5' CTTTCTATTCTCACTCCGCTGAA(NNS)$_{15}$CCGCCTCCACC TCCACC-3' (SEQ ID NO:1);

and

5' GGCCGGTGGAGGTGGAGGCGG(iii)$_{15}$TTCAGCGGAGTGA GAATAGAAAGGTAC 3' (SEQ ID NO:2).

During the synthesis of (NNS)$_{15}$, a mixture consisting of equal amounts of the deoxynucleotides A, C and T, and about 30% more G was used for N, and an equal mixture of C and G for S. Deoxyinosine (i) was used because of its capacity to base pair with each of the four bases A, G, C, and T. J. F. Reidhaar-Olson et al., *Science*, (1988) 24:53.

Alternatively, other base analogs may be used as described by J. Habener et al., *Proc Natl Acad Sci USA* (1988) 85:1735.

Immediately preceding the nucleotide sequence that encodes the random peptide sequence is a nucleotide sequence that encodes alanine and glutamic acid residues. These amino acids were included because they correspond to the first two amino terminal residues of the wild type mature gene III protein of M13, and thus may facilitate producing the fusion protein produced as described below.

Immediately following the random peptide sequence is a nucleotide sequence that encodes 6 proline residues. Thus, the oligonucleotide encodes the following amino acid sequence:

H$_2$N-Ala-Glu-Xaa$_{15}$-Pro$_6$ (SEQ ID NO:3)

Xaa denotes amino acids encoded by the random DNA sequence. As described below, the oligonucleotides were cloned into a derivative of M13 to produce a mature fusion protein having the above amino acid sequence, and following the proline residues, the entire wild type mature gene III.

EXAMPLE 2

(Construction of the Plasmid M13LP67)

The plasmid M13LP67 was used to express the random peptide/gene III fusion protein construct. M13LP67 was derived from M13 mp19 as described in Devlin, PCT 91/18980, incorporated herein by reference in full.

Briefly, M13mp19 was altered in two ways. The first alteration consisted of inserting the marker gene, β-lactamase, into the polylinker region of the virion. This consisted of obtaining the gene by PCR amplification from the plasmid pAc5. The oligonucleotide primers that were annealed to the pAc5 template have the following sequence:

5' GCTGCCCGAGAGATCTGTATATATGAGTAAACTTGG (SEQ ID NO:4)

5' GCAGGCTCGGGAATTCGGGAAATGTGCGCGGAACCC (SEQ ID NO:5)

Amplified copies of the β-lactamase gene were digested with the restriction enzymes BglII and EcoRI, and the replicative form of the modified M13mp19 was digested with Bam HI and EcoRI. The desired fragments were purified by gel electrophoresis, ligated, and transformed into *E. coli* strain DH5 alpha (BRL). *E. coli* transformed with phage that carried the insert were selected on ampicillin plates. The phage so produced were termed JD32.

The plasmid form of the phage, pJD32 (M13mp19Amp$^r$), was mutagenized so that two restriction sites, EagI and KpnI, were introduced into gene III without altering the amino acids encoded in this region. The restriction sites were introduced using standard PCR in vitro mutagenesis techniques as described by M. Innis et al. in "PCR Protocols—A Guide to Methods and Applications" (1990), Academic Press, Inc.

The KpnI site was constructed by converting the sequence, TGTTCC, at position 1611 to GGTACC. The two oligonucleotides used to effect the mutagenesis have the following sequence:

LP159: AAACTTCCTCATGAAAAAGTC (SEQ ID NO:6)

LP162: AGAATAGAAAGGTACCACTAAAGGA (SEQ ID NO:7)

To construct the EagI restriction site, the sequence at position 1631 of pJD32, CCGCTG, was changed to CGGCCG using the following two oligonucleotides:

LP160: TTTAGTGGTACCTTTCTATTCTCACTCG-
GCCGAAACTGT (SEQ ID NO:8)

LP161: AAAGCGCAGTCTCTGAATTTACCG (SEQ ID NO:9)

More specifically, the PCR products obtained using the primers LP159, LP162 and LP160 and LP161 were digested with BspHI and KpnI, and KpnI and AlwNI, respectively. These were ligated with T4 ligase to M13mp19 previously cut with BspHI and AlwNI to yield M13mpLP66. This vector contains the desired EagI and KpnI restriction sites, but lacks the ampicillin resistance gene, β-lactamase. Thus, the vector M13mpLP67, which contains the EagI and KpnI restriction sites and β-lactamase was produced by removing the β-lactamase sequences from pJD32 by digesting the vector with XbaI and EcoRI. The β-lactamase gene was then inserted into the polylinker region of M13mpLP66 which was previously digested with XbaI and EcoRI. Subsequent ligation with T4 ligase produced M13mpLP67, which was used to generate the random peptide library.

EXAMPLE 3

(Production of Phage Encoding Random Peptides)

To produce phage having DNA sequences that encode random peptide sequences, M13LP67 was digested with EagI and KpnI, and ligated to the oligonucleotides produced as described in Example 1 above. The ligation mixture consisted of digested M13LP67 DNA at 45 ng/µL, a 5-fold molar excess of oligonucleotides, 3.6 U/µL of T4 ligase (New England Biolabs), 25 mM Tris, pH 7.8, 10 mM $MgCl_2$, 2 mM DTT, 0.4 mM ATP, and 0.1 mg/mL BSA. Prior to being added to the ligation mixture, the individual oligonucleotides were combined and heated to 95° C. for 5 minutes, and subsequently cooled to room temperature in 15 µL aliquots. Next, the ligation mixture was incubated for 4 hours at room temperature and subsequently overnight at 15° C. This mixture was then electroporated into E. coli as described below.

M13LP67 DNA was electroporated into H249 cells prepared essentially as described by W. Dower et al., Nuc Acids Res (1988) 16:6127. H249 cells are a recA, sup°, F', $kan^R$ derivative of MM294. Briefly, $4 \times 10^9$ H249 cells and 1 µg of M13LP67 DNA were combined in 85 µL of a low conductivity solution consisting of 1 mM HEPES. The cell/M13LP67DNA mixture was positioned in a chilled 0.56 mm gap electrode of a BTX electroporation device (BTX Corp.) and subjected to a 5 millisecond pulse of 560 volts.

Immediately following electroporation, the cells were removed from the electrode assembly, mixed with fresh H249 lawn cells, and plated at a density of about $2 \times 10^5$ plaques per 400 $cm^2$ plate. The next day phage from each plate were eluted with 30 mL of fresh media, PEG precipitated, resuspended in 20% glycerol, and stored frozen at −70° C. About $2.8 \times 10^7$ plaques were harvested and several hundred analyzed to determine the approximate number that harbor random peptide sequences. Using the polymerase chain reaction to amplify DNA in the region that encodes the random peptide sequence, it was determined that about 50–90% of the phage contained a 69 base pair insert at the 5' end of gene III. This confirmed the presence of the oligonucleotides that encode the random peptides sequences. The PCR reaction was conducted using standard techniques and with the following oligonucleotides:

5' TCGAAAGCAAGCTGATAAACCG 3' (SEQ ID NO:10)

5' ACAGACAGCCCTCATAGTTAGCG 3' (SEQ ID NO:11)

The reaction was run for 40 cycles, after which the products were resolved by electrophoresis in a 2% agarose gel. Based on these results, it was calculated that phage from the $2.8 \times 10^7$ plaques encode about $2 \times 10^7$ different random amino acid sequences.

EXAMPLE 4

(Panning Endothelin B Receptor)

Sf9 insect cells ($10^6$), day 1 post infection, bearing $10^5$ endothelin type B receptors per cell, were mixed with $10^{11}$ random peptide library phage in Grace's insect medium (1 mL) with 1% bovine serum albumin. The cells were gently rotated at room temperature (or 4° C.) for 30 minutes. The cells were washed 5× by centrifugation.

Bound phage were eluted with 6M urea, pH 2.2. The eluate was brought to neutral pH using 2M Tris-HCl (pH 10), and the phage amplified by growth as plaques on solid phase agar plates. The phage were then eluted with Tris-buffered saline and concentrated by polyethylene glycol (PEG) precipitation.

For the second round, COS cells ($10^6$), day 1 post transfection, expressing $10^5$ (or more) endothelin type B receptors per cell were incubated at room temperature with $10^{11}$ phage from round 1 for 30 to 60 minutes in minimum essential medium with 1% BSA and 10 mM HEPES. Cells were washed and the phage eluted, amplified, and concentrated as above.

The third round was performed on $ETR_B$-expressing Sf9 cells, as described above for the first round. The yield of phage was then determined, and additional rounds of panning performed for a total of six rounds.

Results: After six rounds of selection, no significant increase in phage yield was observed, which indicates that the phage were not enriched by the procedure. Although no positive results were obtained, no false positives were obtained either: i.e., the procedure did not select any peptides specific for an irrelevant (non)target. This saves a great deal of time if, for some reason, a binding ligand is not present in the library screened.

EXAMPLE 5

(Panning for uPAR)

Peptides having an affinity for urokinase plasminogen activator receptor (UPAR) were identified as follows:

1.) 15mer phage ($2.5 \times 10^{10}$) prepared as described above were selected by coincubation with $10^6$ Sf9 cells expressing full length uPAR ("fluPAR", day 2 post infection) at room temperature for 60 minutes in Grace's medium with 2% nonfat milk. Binding phage were eluted with 6M urea (pH 2.2), the pH neutralized by adding 2M Tris-HCl, and assayed. The yield of binding phage was 0.0013% ($3.3 \times 10^5$ pfu). The phage were amplified on solid agar plates as plaques, eluted with Tris-buffered saline, and precipitated with polyethylene glycol.

2.) The phage resulting from round 1 were reselected on COS cells transfected with fluPAR on day 2 post-infection, using $3.1 \times 10^{11}$ phage on $2 \times 10^5$ COS cells in DMEM with 2% nonfat milk and 10 mM HEPES. The phage were bound, eluted, assayed, and amplified as described in round 1. The yield of binding phage was 0.039% ($1.2 \times 10^8$ pfu).

3.) The phage selected in round 2 were reselected on Sf9 cells expressing fluPAR (day 2 post-infection) as described for round 1 (2.8×10^10 phage on 10^6 Sf9 cells). The yield of binding phage from this round was 5.40% (1.5×10^9 pfu), indicating a substantial enrichment in binding phage. Phage from the urea eluate were cloned, and the DNA isolated and sequenced. Binding by individual phage clones was assayed against Sf9 cells expressing fluPAR, and Sf9 cells expressing substance P receptor (as a control). The results are as follows:

TABLE 1

| Sequence | SEQ ID: | % Recovery uPAR | SPR | Specificity (uPAR/SPR) |
|---|---|---|---|---|
| AECLNGGTAVSNKYFSNIHWCN* | 12 | 6.8 | 0.008 | 850 |
| AESQTGTLNTLFWNTLR | 13 | 2.8 | 0.008 | 350 |
| AEWHPGLSFGSYLWSKT | 14 | 5.7 | 0.034 | 168 |
| AEMHRSLWEWYVPNQSA | 15 | 4.2 | 0.040 | 105 |
| AEPLDLWSLYSLPPLAM | 16 | 6.0 | 0.095 | 63 |
| AESSLWRIFSPSALMMS | 17 | 3.5 | 0.070 | 50 |

TABLE 1-continued

| Sequence | SEQ ID: | % Recovery uPAR | SPR | Specificity (uPAR/SPR) |
|---|---|---|---|---|
| AESSLWTRYAWPSMPSY | 18 | 12.1 | 0.260 | 47 |
| AEPALLNWSFFFNPGLH | 19 | 4.7 | 0.100 | 47 |
| AEPMPHSLNFSQYLWYT | 20 | 2.2 | 0.080 | 28 |
| AESLPTLTSILWGKESV | 21 | 0.5 | 0.022 | 23 |

*Positive control, residues 13–32 of the EGF-like domain of urokinase (not selected from library).

The present invention has been described with reference to specific embodiments. However, this application is intended to cover those changes and substitutions which may be made by those skilled in the art without departing from the spirit and the scope of the appended claims.

What is claimed:

1. A method for selecting a desired compound having a binding affinity for a selected target, wherein said desired compound is present within a biological peptide library, said method comprising:
   (a) contacting said library with a first substrate, wherein said first substrate comprises said target;
   (b) separating peptides which bind to said first substrate from peptides which do not bind to said first substrate, and amplifying said peptides which bind to said first substrate;
   (c) contacting said amplified peptides with a second substrate, wherein said second substrate differs from said first substrate and comprises said target, wherein one of said first and second substrates comprises a cell;
   (d) separating compounds which bind to said second substrate from similar compounds which do not bind to said second substrate, and amplifying said peptides which bind to said second substrate.

2. The method of claim 1, further comprising:
   (e) contacting said amplified peptides from step (d) with said first substrate; and
   (f) separating peptides which bind to said first substrate from peptides which do not bind to said first substrate, and amplifying said peptides which bind to said first substrate.

3. The method of claim 2, wherein steps (c)–(f) are repeated.

4. The method of claim 1, which further comprises:
   (e) contacting said amplified peptides from step (d) with a third substrate, wherein said third substrate differs from said first and second substrates and comprises said target; and
   (f) separating peptides which bind to said third substrate from peptides which do not bind to said third substrate, and amplifying said peptides which bind to said third substrate.

5. The method of claim 4, which further comprises:

(g) contacting said amplified peptides from step (f) with said first substrate;

(h) separating peptides which bind to said first substrate from peptides which do not bind to said first substrate; then repeating steps (c)–(f).

6. The method of claim 1, wherein said target comprises a cell surface receptor.

7. The method of claim 1, wherein one of said first and second substrates comprises a mammalian cell; and the other of said first and second substrates is selected from the group consisting of recombinant insect cells, recombinant yeast, and recombinant bacteria.

8. The method of claim 7, wherein one of said first and second substrates is selected from the group consisting of COS cells, CHO cells, and 293 cells, and the other of said first and second substrates is selected from the group consisting of baculovirus-infected Sf9 cells, *Saccharomyces cerevisae*, and *E. coli*;

wherein both said first and second substrates express said target.

9. The method of claim 1, wherein:

one of said first and second substrates comprises a mammalian cell; and the other of said first and second substrates comprises an inert support having target bound thereto.

10. The method of claim 1, wherein:

one of said first and second substrates is selected from the group consisting of recombinant insect cells, recombinant yeast, and recombinant bacteria; and the other of said first and second substrates comprises an inert support having target bound thereto.

11. A method for selecting a desired compound having a binding affinity for a target, wherein said desired compound is present within a biological peptide library, said method comprising:

(a) contacting said library with a target;

(b) immobilizing said target on a first substrate;

(c) separating peptides which bind to said target or said first substrate from peptides which do not bind to said target or said first substrate, and amplifying said peptides which bind to said target or said first substrate;

(d) contacting said amplified peptides with a second substrate, wherein said second substrate differs from said first substrate in that peptides which bind to one or more non-targets on said first substrate do not also bind to said second substrate, and wherein said second substrate comprises said target; then (e) separating peptides which bind to said second substrate from peptides which do not bind to said second substrate, and amplifying said peptides which bind said to second substrate.

12. A method for selecting a desired compound having a binding affinity for a target, wherein said desired compound is present within a biological peptide library, said method comprising:

(a) contacting said library with a first substrate, wherein said first substrate comprises said target;

(b) separating peptides which bind to said first substrate from peptides which do not bind to said first substrate, and amplifying said peptides which bind to said first substrate;

(c) contacting said amplified peptides with said target in the absence of said first substrate;

(d) immobilizing said target on a second substrate, wherein said second substrate differs from said first substrate in that peptides which bind to one or more non-targets on said first substrate do not also bind to said second substrate; then (e) separating peptides that bind to said target or said second substrate from peptides which do not bind to said target or said second substrate, and amplifying said peptides which bind to said target or said second substrate.

13. A method for identifying a desired compound having a binding affinity for a target, wherein said desired compound is present within a biological peptide library, said method comprising:

(a) contacting said library with a target;

(b) immobilizing said target on a first substrate;

(c) separating peptides which bind to said target or said first substrate from peptides which do not bind to said target or first substrate, and amplifying said peptides which bind to said target or first substrate;

(d) contacting said amplified peptides with said target;

(e) immobilizing said target on a second substrate, wherein said second substrate differs from said first substrate in that peptides which bind to one or more non-targets on said first substrate do not also bind to said second substrate; then (f) separating peptides which bind to said target or said second substrate from peptides which do not bind to said target or second substrate, and amplifying said peptides which bind to said target or said second substrate.

* * * * *